US010803582B2

(12) United States Patent
Hosoi

(10) Patent No.: US 10,803,582 B2
(45) Date of Patent: Oct. 13, 2020

(54) IMAGE DIAGNOSIS LEARNING DEVICE, IMAGE DIAGNOSIS DEVICE, IMAGE DIAGNOSIS METHOD, AND RECORDING MEDIUM FOR STORING PROGRAM

(71) Applicant: NEC CORPORATION, Tokyo (JP)

(72) Inventor: Toshinori Hosoi, Tokyo (JP)

(73) Assignee: NEC CORPORATION, Tokyo (JP)

(*) Notice: Subject to any disclaimer, the term of this patent is extended or adjusted under 35 U.S.C. 154(b) by 107 days.

(21) Appl. No.: 16/315,015

(22) PCT Filed: Jul. 3, 2017

(86) PCT No.: PCT/JP2017/024332
§ 371 (c)(1),
(2) Date: Jan. 3, 2019

(87) PCT Pub. No.: WO2018/008593
PCT Pub. Date: Jan. 11, 2018

(65) Prior Publication Data
US 2019/0311475 A1     Oct. 10, 2019

(30) Foreign Application Priority Data

Jul. 4, 2016  (JP) ................................. 2016-132659

(51) Int. Cl.
*G06T 7/00*     (2017.01)
*G06N 3/08*     (2006.01)
(Continued)

(52) U.S. Cl.
CPC ............ *G06T 7/0012* (2013.01); *A61B 1/045* (2013.01); *A61B 5/7267* (2013.01); *G06N 3/08* (2013.01); *G06T 7/00* (2013.01)

(58) Field of Classification Search
None
See application file for complete search history.

(56) References Cited

U.S. PATENT DOCUMENTS

| 2007/0191677 A1* | 8/2007 | Nishimura ............ A61B 1/042 600/109 |
| 2017/0169567 A1* | 6/2017 | Chefd'hotel ....... G06K 9/00127 |

FOREIGN PATENT DOCUMENTS

| JP | 2000-259598 A | 9/2000 |
| JP | 2006-122502 A | 5/2006 |
| WO | 2015/177268 A1 | 11/2015 |

OTHER PUBLICATIONS

Olympus Corporation of the Americas, "Narrow Band Imaging", Apr. 19, 2016, 8 pages, URL: <http://medical.olympusamerica.com/technology/narrow-band-imaging>.

(Continued)

*Primary Examiner* — Dov Popovici
(74) *Attorney, Agent, or Firm* — Sughrue Mion, PLLC

(57) ABSTRACT

An image diagnosis learning device includes: CNN configuration storage storing a network configuration of a convolutional neural network (CNN); parameter storage storing parameters of a learning subject in the CNN; inappropriate region detection unit that detects, an inappropriate region, in an image for learning in which the diagnosis subject is photographed; and inappropriate region invalidation unit invalidates a unit corresponding to the inappropriate region, among units of an input layer in the network configuration of the CNN to which the image for learning has been input. The image diagnosis learning device further includes loss value calculation unit performs calculation of the CNN by using the parameters in a state where the unit of the input layer, which corresponds to the inappropriate region, has been invalidated, and calculates a loss value; and parameter updating unit updates the parameters in the parameter storage.

10 Claims, 12 Drawing Sheets

(51) Int. Cl.
A61B 1/045 (2006.01)
A61B 5/00 (2006.01)

(56) References Cited

OTHER PUBLICATIONS

Thomas Stehle, et al., "Classification of Colon Polyps in NBI Endoscopy Using Vascularization Features", Proc. of Medical Imaging 2009, Computer-Aided Diagnosis, Feb. 2009, 14 pages, vol. 7260.
Alex Krizhevsky, et al., "ImageNet Classification with Deep Convolutional Neural Networks", Advances in Neural Information Processing Systems, 2012, 9 pages.
Akihiro Tanaka, et al., "Construction of Fingerprint Recognition System on Fast Fourier Transform Preprocessing by Layered Neural Network", IEICE Technical Report, Mar. 10, 2006, pp. 91-96, vol. 105, No. 695.
International Search Report for PCT/JP2017/024332 dated Sep. 26, 2017 [PCT/ISA/210].
Written Opinion for PCT/JP2017/024332 dated Sep. 26, 2017 [PCT/ISA/237].

\* cited by examiner

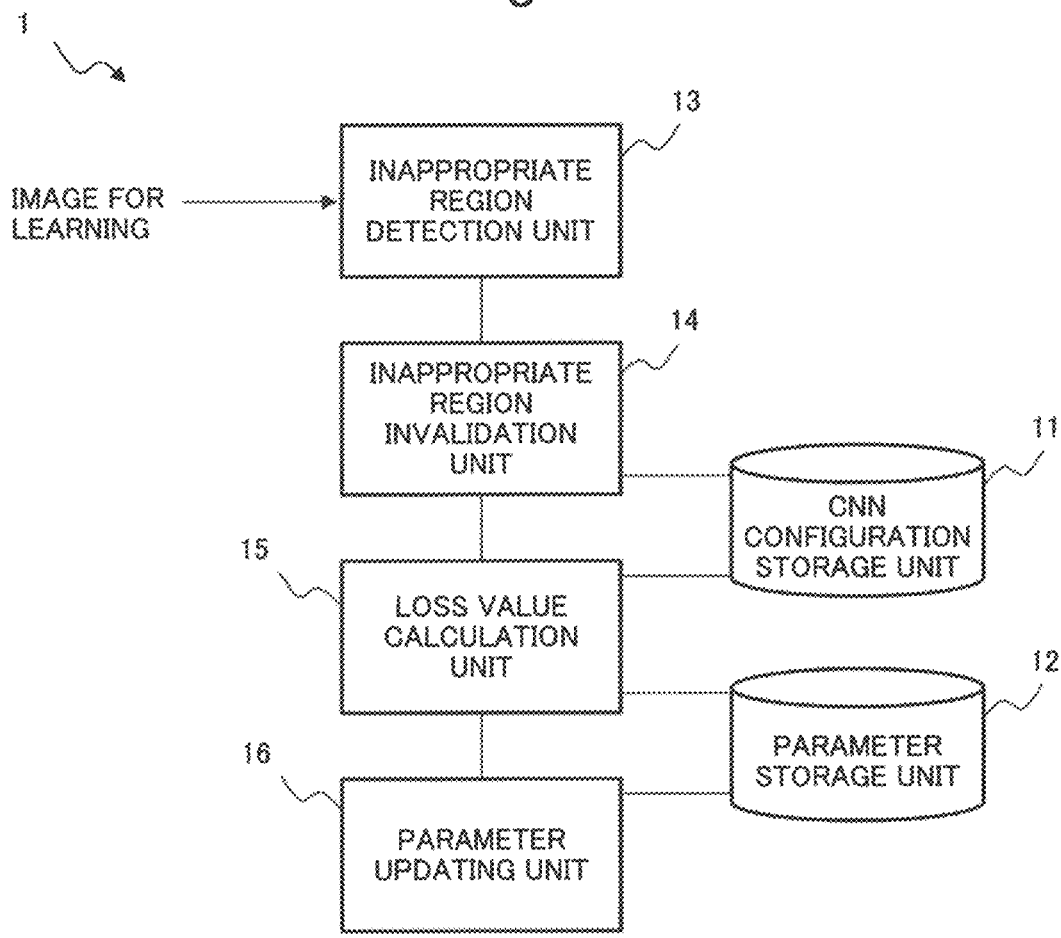
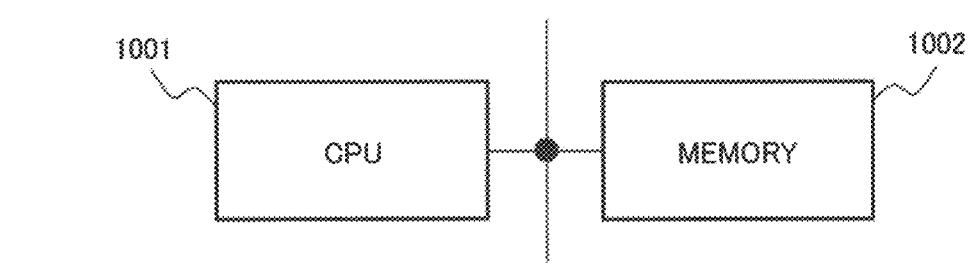

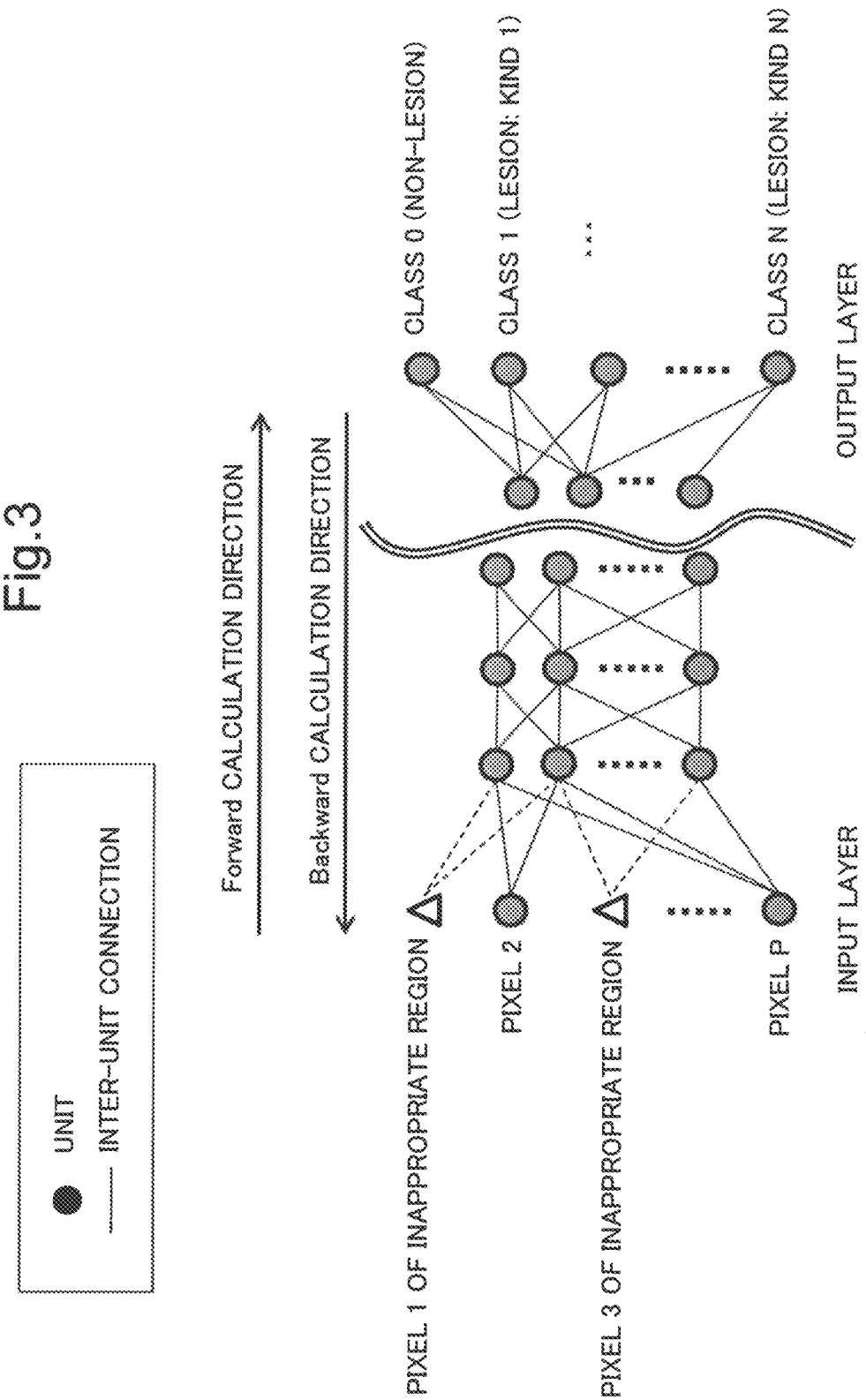

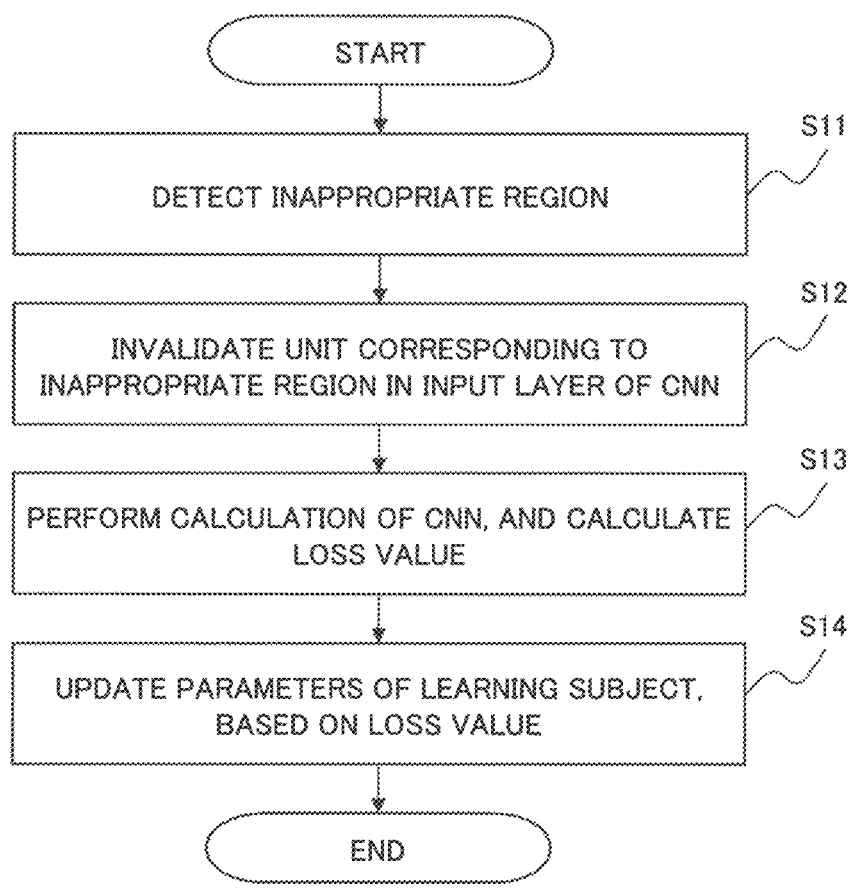

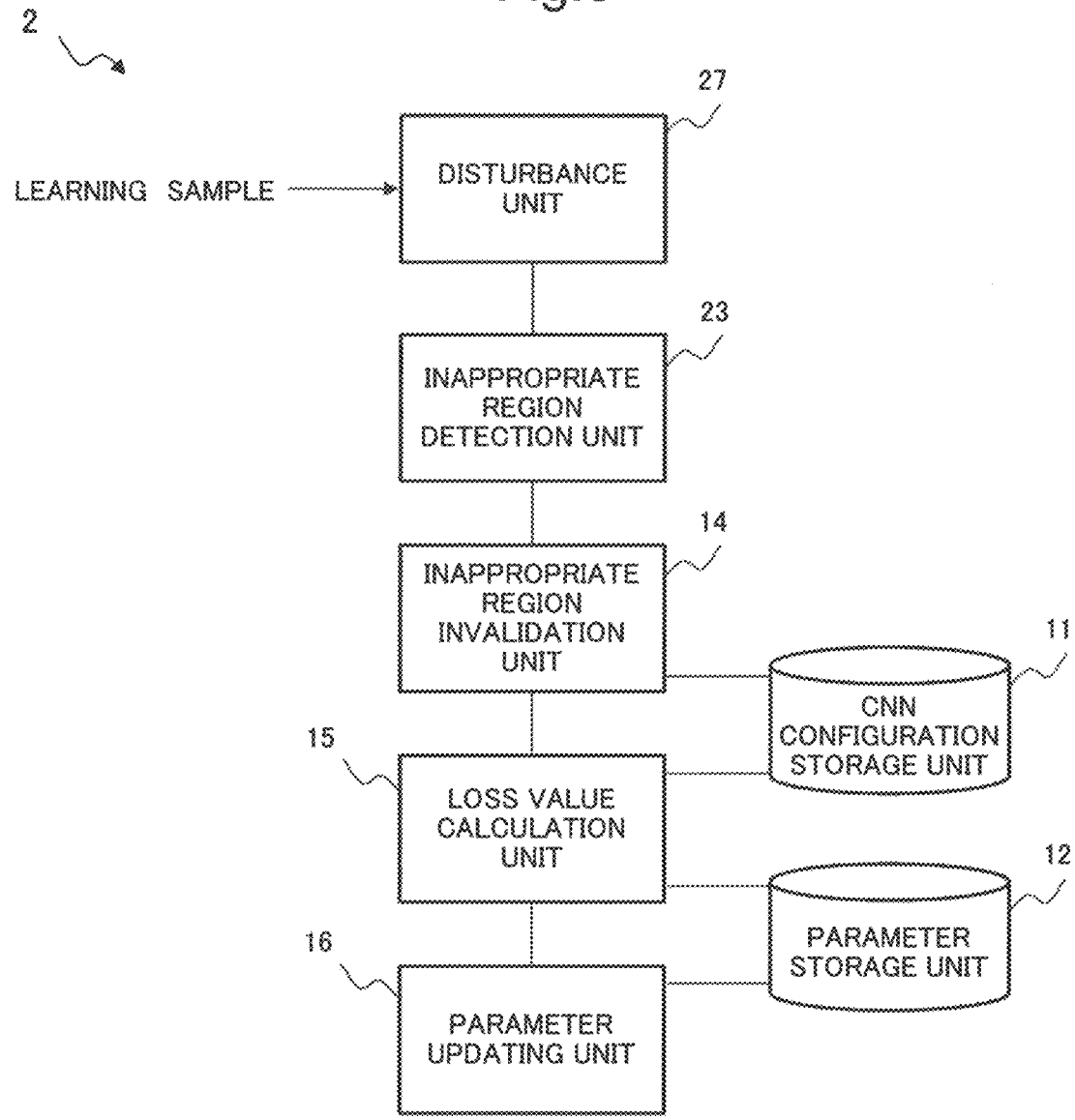

IMAGE DIAGNOSIS LEARNING DEVICE, IMAGE DIAGNOSIS DEVICE, IMAGE DIAGNOSIS METHOD, AND RECORDING MEDIUM FOR STORING PROGRAM

CROSS REFERENCE TO RELATED APPLICATIONS

This application is a National Stage of International Application No. PCT/JP2017/024332, filed on Jul. 3, 2017, which claims priority from Japanese Patent Application No. 2016-132659, filed on Jul. 4, 2016, the contents of all of which are incorporated herein by reference in their entirety.

TECHNICAL FIELD

One aspect of embodiments of the present invention relates to a technique of detecting an abnormal region in a diagnosis subject image in which a diagnosis subject is photographed.

BACKGROUND ART

There is a field in which it is required to detect a region where a diagnosis subject has a possibility of abnormality, in an image in which the diagnosis subject is photographed. Hereinafter, an image in which a diagnosis subject is photographed is also referred to as "diagnosis subject image". In addition, a region where a diagnosis subject has a possibility of abnormality is also referred to as "abnormal region". For example, in a medical examination for discovering a lesion such as a cancer or polyp of a digestive system, a medical specialist performs a work of confirming, by visual observation, an endoscopic image in which a visceral wall surface is photographed by using a digestive endoscope camera. The endoscope camera has a tubular shape. By inserting the endoscope camera from the outside of the body, and by drawing, advancing and rotating the endo scope camera, the visceral wall surface is photographed. Besides, since the inside of the body is dark, photography is performed while illuminating the visceral wall surface with an illuminator provided at a distal end of the endoscope camera.

However, in some cases, due to various factors, a region in which an intended diagnosis subject is not sufficiently photographed exists in the diagnosis subject image. For example, at the time of the above-described photography by the digestive endoscope camera, when an obstruction, such as digested matter remaining in the viscera, hinders the photography, such a work as applying water to the visceral wall surface is performed. In this case, however, since specular reflection of light tends to occur, a shine frequently occurs on the visceral wall surface. To search for a lesion from an endoscopic image including shine parts is a difficult work which requires expertise and highly concentrated attention. In this manner, even the medical specialist may possibly overlook an abnormal region from the diagnosis subject image including a region where an intended diagnosis subject is not sufficiently photographed, unless the medical specialist carefully observes by taking time.

Under the circumstances, there is a method of acquiring a diagnosis subject image by using a special photography method which photographs a diagnosis subject more clearly. For example, there is a photography method in which, when photography is performed by an endoscope camera, lights of a plurality of specific frequencies are radiated on the visceral wall surface, thereby emphasizing a blood vessel or a gland structure in the endoscopic image. This photography method is called Narrow Band Imaging (trademark) (see, e.g. NPL 1). Hereinafter, Narrow Band Imaging is also referred to as NBI. If an endoscopic image by NBI is used, it becomes easier for a doctor to observe a lesion. In this case, however, since the amount of light becomes smaller than in the case of a normal image, it is not practical to usually perform photography by NBI. In another example, after a part that may possibly be a lesion is found, an endoscope camera called "magnifying endoscope", which zooms and photographs the location of this part, may be used.

On the other hand, there is known related art which supports detection of an abnormal region by recognizing the content of a diagnosis subject image by a computer. For example, in the related art of NPL 2, an endoscopic image by NBI is input, and, with respect to a region of a lesion part that was found in advance in this endoscopic image, the stage of disease (adenoma, progressive cancer, etc.) of the region is diagnosed. By making good use of this result, it is expected that the doctor can easily judge the presence/absence of a lesion. In this manner, when the recognition process is performed by using the endoscopic image by NBI as the input, it is known that a relatively high identification precision is obtained. Note that in the related art of NPL 2, a disease is identified by utilizing a feature relating to the shape of a blood vessel. As the feature, information designed by a technological developer is used.

In addition, NPL 3 discloses a method of learning, by using a large volume of real data, the extraction of a feature which is utilized when an abnormal region in a diagnosis subject image is detected by a computer. This is a method utilizing convolutional neural networks (hereinafter, also referred to as CNN) which are a kind of neural network (hereinafter, also referred to as NN). According to NPL 3, it is reported that a higher-precision identification rate can be achieved than in the case of utilizing features designed manually by a technological developer.

Here, the NN includes a learning process and an identification process. Referring to FIG. 14, the outlines of these processes will be described. FIG. 14 is a view representing a network configuration of the NN. In FIG. 14, circles denote units of the NN. In addition, straight lines express connections between the units. The unit calculates an output value x' according to a mathematical expression, $x'=f(w \cdot x + b)$, by using a weight w, a bias b and an activation function f with respect to an input value x. The w and b can take different values with respect to the individual connections between the units. Here, "·" represents a product. In addition, function f ( ) is an arbitrary monotone increasing function. Note that the number of units, and which unit is connected to which unit, are designed in advance by a technological developer. The CNN is configured to be capable of executing an equal process to a general convolution process for an image, by the addition of a restriction that these parameters are partially shared in layers. As intermediate layers of the CNN, many kinds of intermediate layers are known. Examples of such intermediate layers include a Convolution layer, a Pooling layer, and a fully-connected layer (linearly-connected layer).

The example of the NN illustrated in FIG. 14 is a multilayer network configuration. For example, pixel values of an image are input to units 1 to P (P is an integer of 1 or more) of an input layer. The pixel values are passed through units of intermediate layers, and identification results are output from units 1 to N (N is an integer of 1 or more) of an output layer. Class information, which is indicative of a class of an abnormal region of which an identification result is to be obtained, is assigned to each unit of the output layer.

Examples of such class information include classes such as a non-lesion, polyp and cancer. In FIG. 14, the class information may also be called "label", "category" or "teacher signal" in the field of image recognition. In the learning process, many data, which are prepared in advance, are repeatedly input to the input layer, and a calculation based on the parameters of the network is successively executed. This calculation is called "Forward calculation". In addition, the parameters are updated while a calculation is performed in a backward direction so as to minimize a difference (called "loss") between a value of the output layer by the Forward calculation and a target value. This calculation is called "Backward calculation". In the identification process, the Forward calculation is executed by utilizing the parameters which were found by the learning process, and identification results are output. Note that in the CNN executes a convolution operation in the Convolution layer, and executes a sampling process in the Pooling layer. These processes can be regarded as processes for extracting features from an input image. Further, a process in a subsequent layer can be regarded as an identification process. In short, it can also be said that, by learning one CNN, the design of feature extraction (parameters for feature extraction) and identification parameters can be found at the same time.

CITATION LIST

Non Patent Literature

NPL 1: Olympus Corporation of the Americas, "Narrow Band Imaging", [online], [search on Apr. 19, 2016], Internet <http://medical.olympusamerica.com/technology/narrow-band-imaging>

NPL 2: Thomas Stehle, Roland Auer, Alexander Behrens, Jonas Wulff, TilAach, Ron Winograd, Christian Trautwein, Jens Tischendorf, "Classification of Colon Polyps in NBI Endoscopy Using Vascularization Features", Proc. Of Medical Imaging 2009, Computer-Aided Diagnosis. Vol. 7260, 72602S, 2009

NPL 3: Krizhevsky, Alex, Ilya Sutskever, and Geoffrey E. Hinton, "ImageNet classification with deep convolutional neural networks" Advances in neural information processing systems, 2012.

SUMMARY OF INVENTION

Technical Problem

The above-described related art, however, has the following problems.

In the related art of NPL 2, the identification is executed by using the endoscopic image by NBI of NPL 1. In addition, in the related art of NPL 3, the feature capable of identifying the subject is extracted by using the endoscopic image by NBI, in which the blood vessel or gland structure is largely and clearly photographed.

However, as described above, it is not practical to usually perform the photography by NBI of NPL 1. In this manner, when the diagnosis subject image, which was acquired by a normal photography method that is not implemented by a special function, is used as an input, it is difficult to precisely detect the abnormal region by using the related art of NPL 2. In addition, when the diagnosis subject image, which was acquired by a normal photography method without a special function, is used as an input, it is difficult to extract the feature capable of identifying the subject, even with use of the related art of NPL 3. Moreover, in many cases, the diagnosis subject image includes a region in which an intended diagnosis subject is not sufficiently photographed, such as the above-described shine part. When such a diagnosis subject image is used as an input, it is more difficult to extract the feature capable of identifying the subject, by using the related art of NPL 3. As a result, even if the related art of NPL 3 is used, it is difficult to precisely detect an abnormal region.

One aspect of embodiments of the present invention has been made in order to solve the above problems. Specifically, the one aspect of object of the invention is to provide a technique of more precisely detecting an abnormal region, even when a region in which an intended diagnosis subject is not sufficiently photographed is included in a diagnosis subject image which is acquired by a normal photography method that is not implemented by a special function.

Solution to Problem

An image diagnosis learning device according to one aspect of embodiments of the present invention includes: CNN configuration storage means for storing a network configuration of a convolutional neural network (CNN); parameter storage means for storing parameters of a learning subject in the CNN; inappropriate region detection means for detecting, based on a predetermined criterion, an inappropriate region which is a region inappropriate for identification of an abnormal region where a diagnosis subject has a possibility of abnormality, in an image for learning in which the diagnosis subject is photographed; and inappropriate region invalidation means for invalidating a unit corresponding to the inappropriate region, among units of an input layer in the network configuration of the CNN to which the image for learning has been input.

The image diagnosis learning device further includes loss value calculation means for performing calculation of the CNN by using the parameters in a state where the unit of the input layer, which corresponds to the inappropriate region, has been invalidated, and for calculating a loss value based on a result of the calculation and information, the information indicating abnormality of the diagnosis subject and given to the image for learning in advance; and parameter updating means for updating the parameters in the parameter storage means, based on the loss value.

An image diagnosis device according to one aspect of embodiments of the present invention includes: parameter storage means for storing the parameters of the CNN, which were updated by applying the above image diagnosis learning device to one or a plurality of images for learning; CNN configuration storage means for storing a network configuration of the CNN used by the image diagnosis learning device when the parameters were updated; and CNN identification means for inputting information based on the diagnosis subject image, in which the diagnosis image is photographed, to the CNN, and performing calculation, thereby identifying an abnormal region where the diagnosis subject has a possibility of abnormality in the diagnosis subject image.

One aspect of embodiments of the present invention provides a method in which a computer device executes: detecting, based on a predetermined criterion, an inappropriate region which is a region inappropriate for identification of an abnormal region where a diagnosis subject has a possibility of abnormality, in an image for learning in which the diagnosis subject is photographed; invalidating a unit corresponding to the inappropriate region, among units of an input layer in a network configuration of a convolutional neural network (CNN) to which the image for learning has been input; performing calculation of the CNN in a state where the unit of the input layer, which corresponds to the inappropriate region, has been invalidated, and calculating a loss value based on a result of the calculation and information, the information indicating abnormality of the diagnosis subject and given to the image for learning in advance; and updating parameters of a learning subject in the CNN, based on the loss value.

A recording medium according to one aspect of embodiments of present invention stores a program. The program causes a computer device to execute: detecting, based on a predetermined criterion, an inappropriate region which is a region inappropriate for identification of an abnormal region where a diagnosis subject has a possibility of abnormality, in an image for learning in which the diagnosis subject is photographed; invalidating a unit corresponding to the inappropriate region, among units of an input layer in a network configuration of a convolutional neural network (CNN) to which the image for learning has been input; performing calculation of the CNN in a state where the unit of the input layer, which corresponds to the inappropriate region, has been invalidated, and calculating a loss value based on a result of the calculation and information, the information indicating abnormality of the diagnosis subject and given to the image for learning in advance; and updating parameters of a learning subject in the CNN, based on the loss value.

One aspect of embodiments of the present invention provides another method in which a computer device executes, by using the parameters of the CNN, which were updated by executing the above method on one or a plurality of images for learning, and a network configuration of the CNN used when the parameters were updated, inputting information based on the diagnosis subject image, in which the diagnosis image is photographed, to the CNN, and performing calculation, thereby identifying an abnormal region where the diagnosis subject has a possibility of abnormality in the diagnosis subject image.

A recording medium stores a program. The program causes a computer device to execute, by using the parameters of the CNN, which were updated by causing the computer device to execute the program stored in the recording medium on one or a plurality of images for learning, and a network configuration of the CNN used when the parameters were updated, inputting information based on the diagnosis subject image, in which the diagnosis image is photographed, to the CNN, and performing calculation, thereby identifying an abnormal region where the diagnosis subject has a possibility of abnormality in the diagnosis subject image.

Advantageous Effects of Invention

An example embodiment of the present invention may provide a technique of more precisely detecting an abnormal region, even when a region in which an intended diagnosis subject is not sufficiently photographed is included in a diagnosis subject image which is acquired by a normal photography method that is not implemented by a special function.

BRIEF DESCRIPTION OF DRAWINGS

FIG. 1 is a block diagram illustrating a configuration of an image diagnosis learning device as a first example embodiment;

FIG. 2 is a view illustrating an example of a hardware configuration of the image diagnosis learning device as the first example embodiment;

FIG. 3 is a view for schematically describing invalidation of an inappropriate region in the first example embodiment;

FIG. 4 is a flowchart for describing an operation of the image diagnosis learning device as the first example embodiment;

FIG. 5 is a block diagram illustrating a configuration of an image diagnosis learning device as a second example embodiment;

EXAMPLE EMBODIMENT

Figure 6:
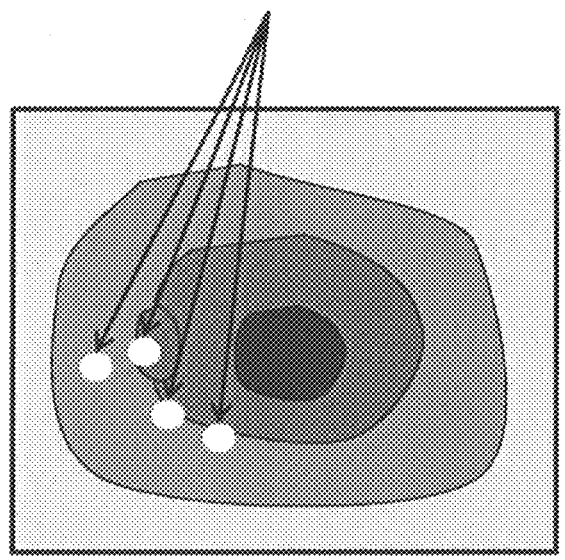
FIG. 6 is a view schematically illustrating an example of an endoscopic image in which a shine occurs in the second example embodiment.

Hereinafter, example embodiments of the present invention will be described in detail with reference to the accompanying drawings.

First Example Embodiment

FIG. 1 illustrates a functional block configuration of an image diagnosis learning device 1 as a first example embodiment. In FIG. 1, the image diagnosis learning device 1 includes a CNN configuration storage unit 11, a parameter storage unit 12, an inappropriate region detection unit 13, an inappropriate region invalidation unit 14, a loss value calculation unit 15 and a parameter updating unit 16. The image diagnosis learning device 1 is a device which learns parameters used in a CNN that identifies an abnormal region in an image in which a diagnosis subject is photographed. Here, it is assumed that the abnormal region refers to a region where a diagnosis subject in an image in which the diagnosis subject is photographed may possibly have abnormality.

Here, the image diagnosis learning device 1 can be composed of hardware elements as illustrated in FIG. 2. In FIG. 2, the image diagnosis learning device 1 is composed of a computer device including a central processing unit (CPU) 1001 and a memory 1002. The memory 1002 is composed of a random access memory (RAM), a read only memory (ROM), an auxiliary storage device (hard disk or the like), etc. In this case, the CNN configuration storage unit 11 and parameter storage unit 12 are composed of the memory 1002. In addition, the inappropriate region detection unit 13, inappropriate region invalidation unit 14, loss value calculation unit 15 and parameter updating unit 16 are composed of the CPU 1001 which reads in a computer program stored in the memory 1002 and executes the computer program. Note that the hardware configuration of the image diagnosis learning device 1 and each functional block thereof is not limited to the above-described configuration.

The CNN configuration storage unit 11 stores information representing a network configuration of a convolutional neural network (CNN). The information representing the network configuration may include, for example, an image size and the number of channels of an input layer; kinds, sizes and process parameters of a plurality of intermediate layers; and the number of units of an output layer. The kinds of intermediate layers include a Convolution layer, a Pooling layer and a fully-connected layer (linearly-connected layer), as described above. In addition, examples of the process parameters are as follows. For instance, there are parameters such as a size (width, height, channel number) of a Convolution kernel, a stride width at a time of Convolution calculation, and the presence/absence of a process of padding, with specific values, the image ends in order to adjust the size at the time of Convolution calculation.

The parameter storage unit 12 stores parameters of a learning subject in the above-described CNN. The parameters of the learning subject include, for example, the weight and bias used in the calculation of each unit. These parameters are regarded as parameters for extracting the feature of an abnormal region, or as parameters for identifying an abnormal region by using this feature.

Note that the default values of the parameters stored in the parameter storage unit 12 may be random numbers. Alternatively, the default values of the parameters may be values which were learned for the purpose of other image recognition applications. For example, when the default values of the parameters are parameters for recognizing general objects such as animals or vehicles, or parameters learned for identifying a pattern in an image, a high learning effect can be obtained in some cases, and this is useful.

The inappropriate region detection unit 13 detects, based on a predetermined criterion, an inappropriate region that is a region inappropriate for identifying an abnormal region, in an image for learning in which a diagnosis subject is photographed. As the inappropriate region, for example, a region in which an intended diagnosis subject is not sufficiently photographed is applied. In this case, the inappropriate region detection unit 13 may detect, as an inappropriate region, a region which meets a condition under which it can be determined that an intended diagnosis subject is not sufficiently photographed.

Note that the image for learning may be, for example, a partial image of an image in which a diagnosis subject is photographed. In addition, it is assumed that information indicative of abnormality relating to the photographed diagnosis subject is added to the image for learning as correct information. The information indicative of abnormality may be, for example, information indicating whether there is a possibility of abnormality or not. In addition, the information indicative of abnormality may be, for example, information indicative of the kind of abnormality when there is a possibility of abnormality. Besides, the information indicative of abnormality may be, for example, information indicative of the degree of the possibility of abnormality. However, the content of information indicative of abnormality is not limited to these.

Figure 14:
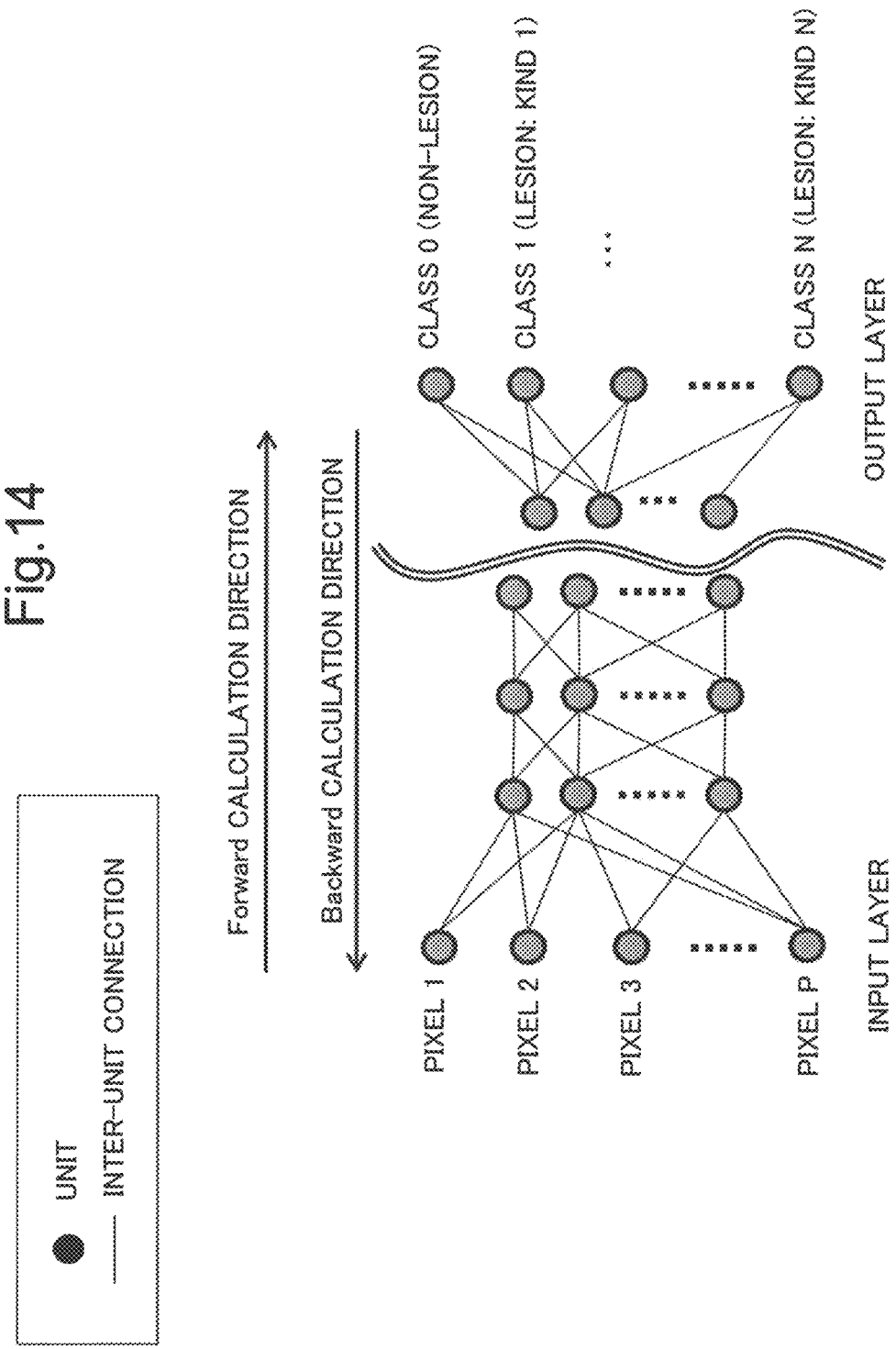
FIG. 14 is a view schematically illustrating a network configuration of a neural network in related art.

The inappropriate region invalidation unit 14 invalidates a unit corresponding to an inappropriate region among units of an input layer in a network configuration of a CNN to which an image for learning is input. The network configuration of the CNN, to which the image for learning is input, is stored in the above-described CNN configuration storage unit 11. Referring now to a schematic view of FIG. 3, the invalidation of the unit of the input layer, which corresponds to the inappropriate region, will be described. Here, it is assumed that the network configuration of the CNN is the configuration illustrated in FIG. 14. In addition, it is assumed that the respective pixel values of the image for learning are input to the input layer of the CNN. In this case, as illustrated in FIG. 3, units, to which pixels included in an inappropriate region are input, are invalidated. Triangular marks in the Figure represent the invalidated units. In this example, a pixel 1 and a pixel 3 are included in the inappropriate region. Thus, the units to which the pixel 1 and pixel 3 are input are invalidated. In the calculation of the CNN, a connection from an invalidated unit to a unit of a neighboring layer is treated as being absent. A broken line in the Figure represents a connection which is treated as being absent. Note that invalidation by the inappropriate region invalidation unit 14 is temporary invalidation. Specifically, even if the inappropriate region invalidation unit 14 invalidates some units of the input layer with respect to a certain image for learning, when the inappropriate region invalidation unit 14 processes some other different image for learning, the inappropriate region invalidation unit 14 first releases the invalidation of the invalidated units. Thereafter, the inappropriate region invalidation unit 14 may newly invalidate a unit of the input layer, which corresponds to an inappropriate region in this image for learning.

The loss value calculation unit 15 calculates, by using parameters, a loss value for the learning of the CNN, in a state in which the units of the input layer, which correspond to the inappropriate region, are invalidated. Specifically, in the state in which the units of the input layer, which correspond to the inappropriate region, are invalidated, the loss value calculation unit 15 executes Forward calculation by applying the parameters stored in the parameter storage unit 12. Then, the loss value calculation unit 15 calculates a loss value based on the result of the calculation and the information, the information indicating abnormality and given to the image for learning in advance.

Here, the loss value is an index for optimization, which is calculated at the time of learning of the neural network, and an arbitrary index is applicable. An example of a widely used loss value is as follows: a numeral value group (calculation result), which is output by Forward calculation, is converted to a real value which can take a value in a range of between 0 and 1, by using a SoftMax function, and a difference between the real value and a correct class that is set to 1.0 is calculated as a loss value. Note that the above-described "information which indicates abnormality and which has been given to the image for learning in advance" is information indicative of abnormality of a correct answer, and corresponds to 1.0 of the correct class. However, the calculation method of the loss value is not limited to this.

The parameter updating unit 16 updates, based on the loss value, the parameters of the learning subject, which are stored in the parameter storage unit 12. The parameters to be updated are, for example, the weight and bias, as described above. In addition, for example, the parameter updating unit 16 may update the parameters so as to minimize the loss, by using a cumulative value of loss values which were calculated with respect to a plurality of images for learning. Here, the plural images for learning may be a plurality of partial images of an image in which a diagnosis subject is photographed. For instance, a stochastic descent method or the like is applicable as the minimization (optimization) method in this case. However, the minimization method in this case is not limited to this method, and a discretionarily chosen method is applicable.

The operation of the image diagnosis learning device 1 with the above-described configuration will be described with reference to FIG. 4.

In FIG. 4, to start with, the inappropriate region detection unit 13 detects an inappropriate region from the image for learning, based on a predetermined criterion (step S11).

Next, the inappropriate region invalidation unit 14 invalidates a unit corresponding to the inappropriate region among the units of the input layer of the CNN (step S12).

Subsequently, the loss value calculation unit 15 executes calculation of the CNN in the state in which the unit of the input layer, which corresponds to the inappropriate region, is invalidated. Then, the loss value calculation unit 15 calculates the loss value, based on the result of the calculation and the information which indicates the abnormality, and which has been given to the image for learning in advance (step S13).

Next, the parameter updating unit 16 updates the parameters of the learning subject, based on the calculated loss value (step S14).

By the above, the image diagnosis learning device 1 terminates the operation.

Next, the advantageous effects of the first example embodiment will be described.

The image diagnosis learning device as the first example embodiment can more precisely detect an abnormal region, even when a region in which an intended diagnosis subject is not sufficiently photographed is included in an image in which the diagnosis subject is photographed by a normal photography method that is not implemented by a special function.

The reason for this is described. In the present example embodiment, the inappropriate region detection unit detects, based on a predetermined criterion, an inappropriate region that is a region inappropriate for identifying an abnormal region, in an image for learning in which a diagnosis subject is photographed. Then, the inappropriate region invalidation unit invalidates a unit corresponding to the inappropriate region among the units of the input layer of the CNN, based on the network configuration of the CNN to which the image for learning is input. Subsequently, the loss value calculation unit executes the calculation of the CNN in the state in which the unit of the input layer, which corresponds to the inappropriate region, is invalidated. Then, the loss value calculation unit calculates the loss value based on the result of the calculation of the CNN and the information, the information indicating the abnormality of the correct answer and given to the image for learning in advance. Further, the parameter updating unit updates the parameters of the learning subject in the CNN, based on the loss value. The above is the reason.

In this manner, the present example embodiment determines the parameters of the learning subject in the CNN, based on the image for learning. Thus, the present example embodiment automatically extracts the feature, which is sufficient for identifying the abnormal region, from even the image for learning which was acquired from the image obtained by the photography method that is not implemented by a special function. Moreover, the present example embodiment automatically detects the inappropriate region in which the intended diagnosis subject is not sufficiently photographed, and learns the parameters of the CNN by invalidating the inappropriate region. Thus, the present example embodiment enables the CNN to precisely perform learning, while suppressing the influence of the inappropriate region. Furthermore, by executing operations on a greater number of images for learning, the present example embodiment can automatically extract the feature which enables identification with higher precision, and can learn the parameters. As a result, the present example embodiment can provide parameters with higher precision to the CNN which identifies the abnormal region in the image in which the diagnosis subject is photographed, and enables the detection of the abnormal region with higher precision.

Second Example Embodiment

Next, a second example embodiment will be described in detail with reference to the accompanying drawings. In the present example embodiment, a visceral wall surface is applied as a diagnosis subject. In addition, as an image for learning, an image based on an endoscopic image, in which a visceral wall surface is photographed by an endoscope camera, is applied. Note that in the drawings which are referred to in the description of the present example embodiment, the identical configuration and similarly operating steps to the first example embodiment are denoted by the identical reference signs, and a detailed description thereof in the present example embodiment is omitted.

To begin with, FIG. 5 illustrates a configuration of an image diagnosis learning device 2 as the second example embodiment. In FIG. 5, the image diagnosis learning device 2 differs from the image diagnosis learning device 1 as the first example embodiment, in that the image diagnosis learning device 2 includes an inappropriate region detection unit 23 in place of the inappropriate region detection unit 13, and further includes a disturbance unit 27. Note that the image diagnosis learning device 2 and the functional blocks thereof can be composed of similar hardware elements to the image diagnosis learning device 1 as the first example embodiment described with reference to FIG. 2. However, the hardware configuration of the image diagnosis learning device 2 and the functional blocks thereof is not limited to the above-described configuration.

The disturbance unit 27 generates an image for learning, by executing a disturbance process on a learning sample of an endoscopic image. The disturbance process is a process of imparting minute variations with respect to a position, a scale, a rotational angle, etc.

For example, a patch image, which is a division of an endoscopic image, is input to the disturbance unit 27. The patch image is a partial image included in the endoscopic image. In addition, it is assumed that lesion class information indicative of lesion classes is given as correct information to each of patch images. In this case, the disturbance unit 27 generates, as an image for learning, an image acquired by executing the disturbance process on such a patch image.

Note that the lesion class information may be, for example, information representing either a lesion or a non-lesion. In this case, a numerical value "1" may be given to a patch image including a lesion as the lesion class information indicative of "lesion". On the other hand, a numerical value "0" may be given to a patch image not including a lesion as the lesion class information indicative of "non-lesion".

Besides, for example, the lesion class information may be information representing either the kind 1~n of lesion (n is a positive integer of 2 or more) or a non-lesion. In this case, a numerical value "i" may be given to a patch image including a lesion of the kind i (i is an integer of 1~n) as the lesion class information indicative of "lesion part (kind i)". On the other hand, a numerical value "0" may be given to a patch image not including a lesion as the lesion class information indicative of "non-lesion".

Figure 7:
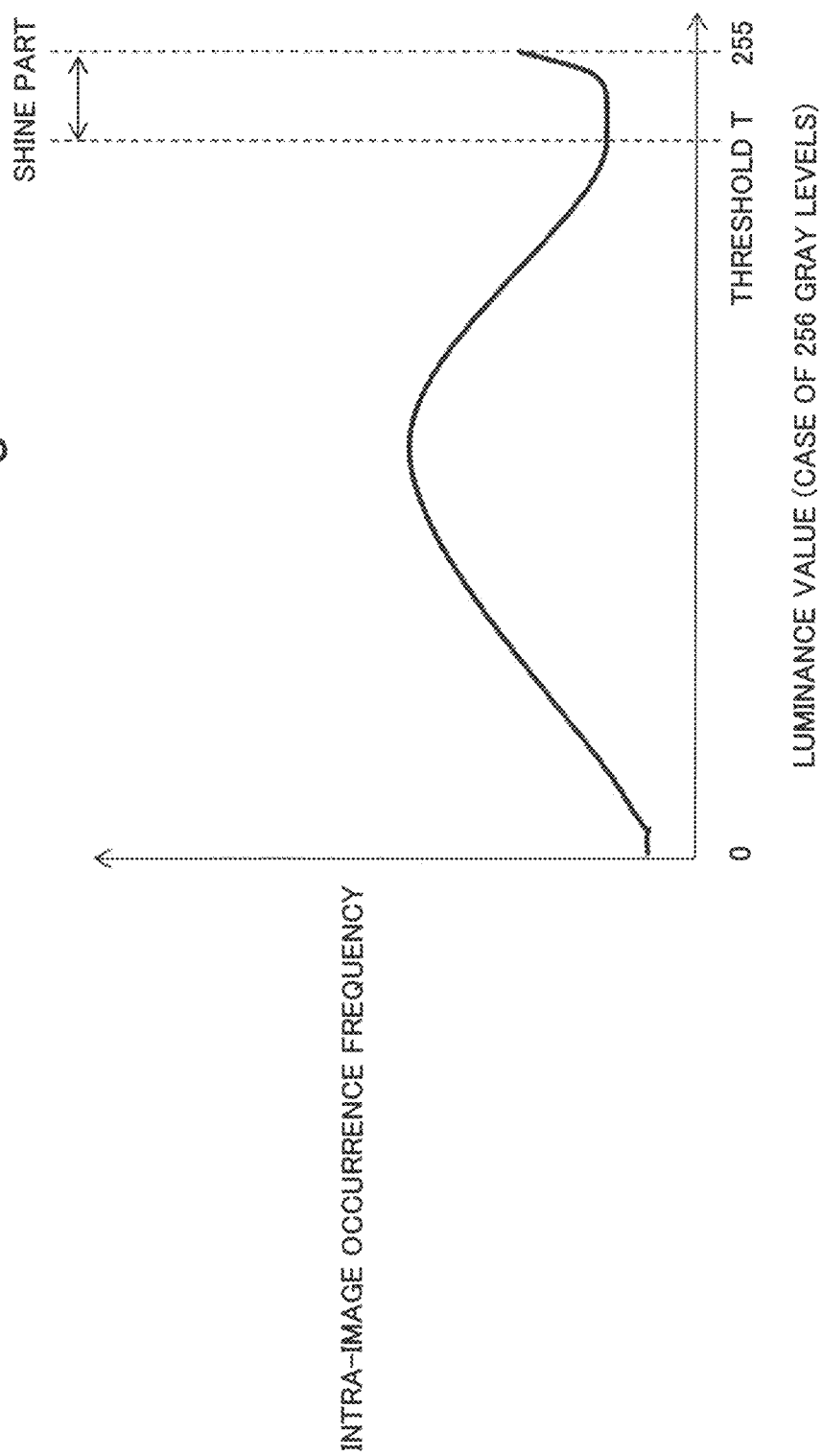
FIG. 7 is a view illustrating an example of a luminance histogram of an endoscopic image in which a shine occurs in the second example embodiment.

The inappropriate region detection unit 23 detects a shine part as an inappropriate region from the image for learning. As described above, the shine part occurs when such a work as applying water to the visceral wall surface is performed at the time of photography by the endoscope camera. The method of detecting a shine part may be an arbitrary method. For example, the inappropriate region detection unit 23 may detect a shine part by executing a threshold process on a luminance value. The detection of a shine part with use of a luminance value will now be described with reference to FIG. 6 and FIG. 7. FIG. 6 is a view schematically illustrating an example of an endoscopic image in which a shine occurs. As illustrated in FIG. 6, when a shine occurs on the visceral wall surface, shine parts in the endoscopic image become white with high luminance. In addition, FIG. 7 is a view illustrating an example of a luminance histogram of an endoscopic image in which a shine occurs. As illustrated in FIG. 7, in the luminance distribution histogram, a luminance value of a shine part becomes extremely high. Specifically, the inappropriate region detection unit 23 can determine that a pixel with a luminance exceeding a threshold is a pixel of a shine part. In addition, the inappropriate region detection unit 23 may determine that a partial region, in which an occurrence rate of a luminance value higher than a threshold meets a predetermined criterion, is a shine part. Besides, the inappropriate region detection unit 23 may detect a shine part by utilizing a process of searching for an isolated point at which a pixel of interest has an extremely high luminance, compared to peripheral pixels.

The operation of the image diagnosis learning device 2 with the above-described configuration will be described with reference to FIG. 8. Note that in the learning process of a neural network, a method of selecting a subset from a learning data set and updating parameters so as to minimize a cumulative value of loss calculated from the subset is widely used in order to obtain the effect of enhancing identification precision. Here, a description is given of an operation example using a learning data set which is composed of patch images which are cut out of an endoscopic image and to which lesion class information is given, and a subset selected from the learning data set.

The information of the learning data set and subset may be stored in the memory 1002. In this case, the image diagnosis learning device 2 may read in the information of the learning data set and subset from the memory 1002, and may execute the operation to be described below.

In addition, the size of the patch image may be an arbitrary size. For example, when each of the number of pixels in width and the number of pixels in height is 256, and the number of RGB components of colors is three (=three channels), the number of units of the input layer of the CNN is 256×256×3. In addition, when lesion classes to be identified are three, namely "non-lesion", "lesion (adenoma)" and "lesion (progressive cancer)", the number of units of the output layer is three.

Besides, the network configuration of the CNN may be, for example, a network configuration in which a plurality of sets, each including a plurality of Convolution layers and one Pooling layer, are connected.

In the operation below, however, the number of lesion classes to be identified, the size of the patch image, the numbers of units of the input layer and output layer of the CNN, and the network configuration are not limited to the examples described above.

Figure 8:
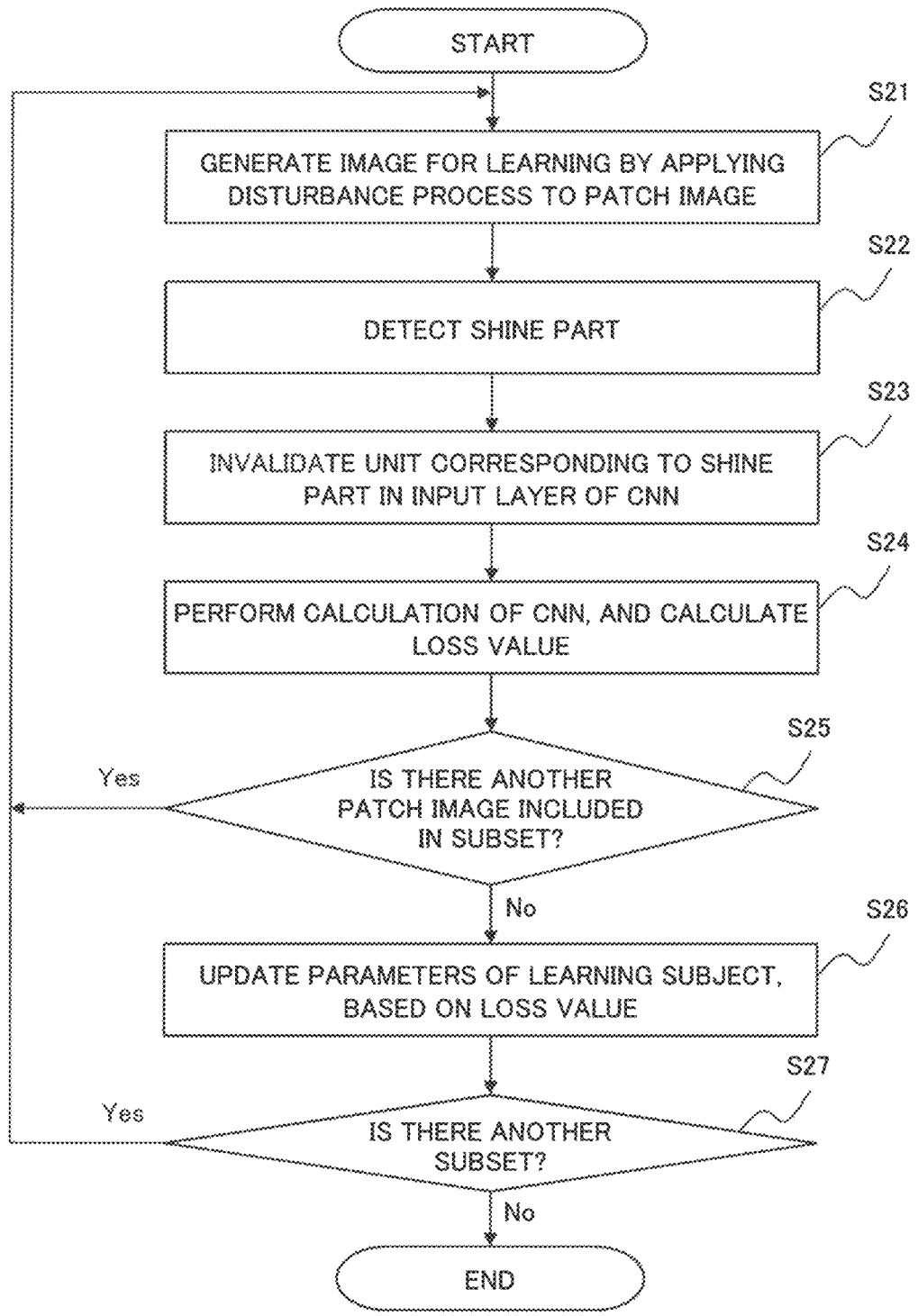
FIG. 8 is a flowchart for describing an operation of the image diagnosis learning device as the second example embodiment.

In FIG. 8, to start with, the disturbance unit 27 inputs therein one of patch images included in the subset, and generates an image for learning, in which a position, scale, rotation, and the like are disturbed (step S21). For example, the disturbance unit 27 may acquire a patch image which is created with a relatively large size, and may cut out, from the acquired patch image, an image, on which the disturbance was applied, as an image for learning.

Next, the inappropriate region detection unit 23 detects, from the image for learning, a shine part as an inappropriate region (step S22).

Subsequently, the inappropriate region invalidation unit 14 operates substantially similarly to the step S12 in the first example embodiment, and temporarily invalidates a unit corresponding to the inappropriate region in the input layer of the CNN to which the image for learning was input. Here, the inappropriate region invalidation unit 14 temporarily invalidates a unit corresponding to the shine part (step S23).

Next, the loss value calculation unit 15 operates substantially similarly to the step S13 in the first example embodiment, and executes Forward calculation of the CNN. Here, the loss value calculation unit 15 executes Forward calculation of the CNN in the state in which the unit of the input layer, which corresponds to the shine part, is temporarily invalidated. Then, the loss value calculation unit 15 calculates the loss value by using the result of the calculation and the lesion class information of the correct answer, which has been given to the image for learning (step S24).

Subsequently, if there is another patch image included in the subset (Yes in step S25), the image diagnosis learning device 2 repeats the process from step S21.

On the other hand, if there is no other patch image included in the subset (No in step S25), the parameter updating unit 16 executes a process of updating the parameters of the learning subject. Specifically, the parameter updating unit 16 may update the weight and bias, based on a cumulative value of loss values calculated with respect to the images for learning included in the subset (step S26).

Next, if there is another subset (Yes in step S27), the image diagnosis learning device 2 repeats the process from step S21.

On the other hand, if there is no other subset (No in step S27), the image diagnosis learning device 2 terminates the operation.

Note that the image diagnosis learning device 2 may execute similar operations for other learning data sets, and may terminate the operation at a time point when the updated loss value or identification error rate has no longer decreased.

By the above, the description of the operation of the image diagnosis learning device 2 ends.

Next, the advantageous effects of the second example embodiment will be described.

The image diagnosis learning device as the second example embodiment can more precisely detect a candidate for a lesion part, even when a shine part is included in an endoscopic image acquired by a normal photography method which is not implemented by a special function such as an NBI endoscope or a magnifying endoscope.

The reason for this is described. The reason is that the present example embodiment includes the following configuration in addition to the similar configuration to the first example embodiment. Specifically, the disturbance unit generates the image for learning by executing the disturbance process on the patch image which is a division of the endoscopic image and to which the lesion class information is given. Then, the inappropriate region detection unit detects a shine part as an inappropriate region from the image for learning.

Thereby, the present example embodiment updates the weight and bias, which constitute the CNN as the parameters for feature extraction, based on the set of images for learning which are based on the endoscopic image. Thus, even with a general endoscopic image acquired not by an NBI endoscope or a magnifying endoscope, it is possible to automatically extract the feature which is sufficient for identification between a normal region of a visceral wall surface and an abnormal region with abnormality, i.e. a possibility of a lesion part.

Furthermore, since the present example embodiment learns the parameters of the CNN by automatically detecting a shine part and invalidating the shine part, the present example embodiment enables the CNN to perform learning, while suppressing the influence of the abnormal value occurring at the shine part. Specifically, in the present example embodiment, the parameters can be learned with no adverse effect, even from such an image for learning that a shine part is included in an endoscopic image.

As a result, an identification device by the CNN, which uses the parameters learned by the present example embodiment, can more exactly detect a candidate for a lesion part, even with an endoscopic image acquired not by a special function.

Note that the present example embodiment can be implemented without the disturbance unit. However, since the disturbance unit disturbs shine parts by executing the disturbance process, the disturbance unit can bring about such an advantageous effect that the parameters can be learned by further suppressing the adverse effect due to shine parts, without the shine parts being unevenly distributed. This advantageous effect by the disturbance unit becomes particularly conspicuous in the case of the operation with use of a small number of learning data sets.

Third Example Embodiment

Next, a third example embodiment will be described in detail with reference to the accompanying drawings. In the present example embodiment, a description is given of an example of an image diagnosis device which identifies an abnormal region in a diagnosis subject image, by using the parameters of the CNN which were updated by the first example embodiment. Note that the diagnosis subject image refers to an image in which a diagnosis subject is photographed, and to an image of a subject with respect to which an abnormal region is to be identified.

Figure 9:
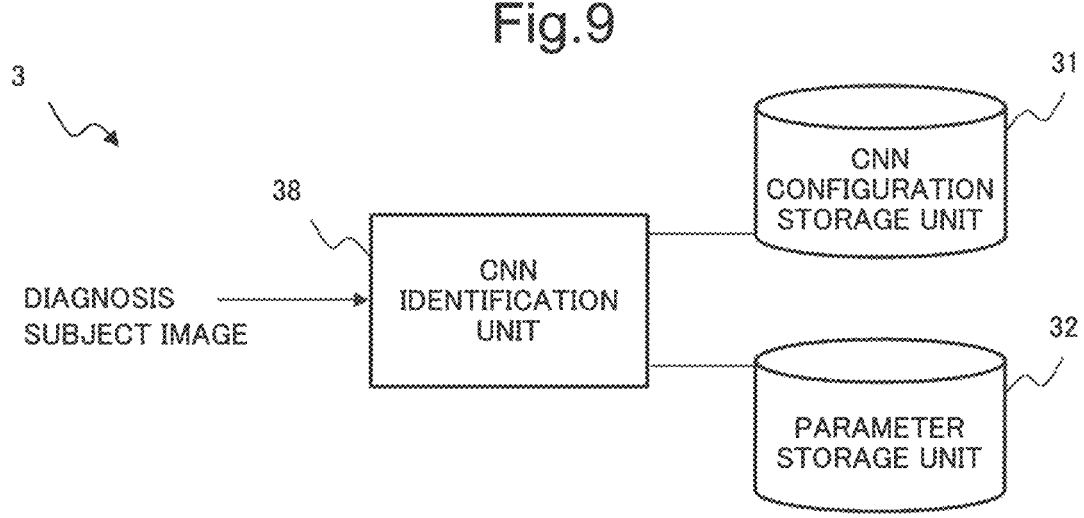
FIG. 9 is a block diagram illustrating a configuration of an image diagnosis device as a third example embodiment.

To begin with, FIG. 9 illustrates a configuration of an image diagnosis device 3 as the third example embodiment. In FIG. 9, the image diagnosis device 3 includes a CNN configuration storage unit 31, a parameter storage unit 32 and a CNN identification unit 38.

Figure 10:
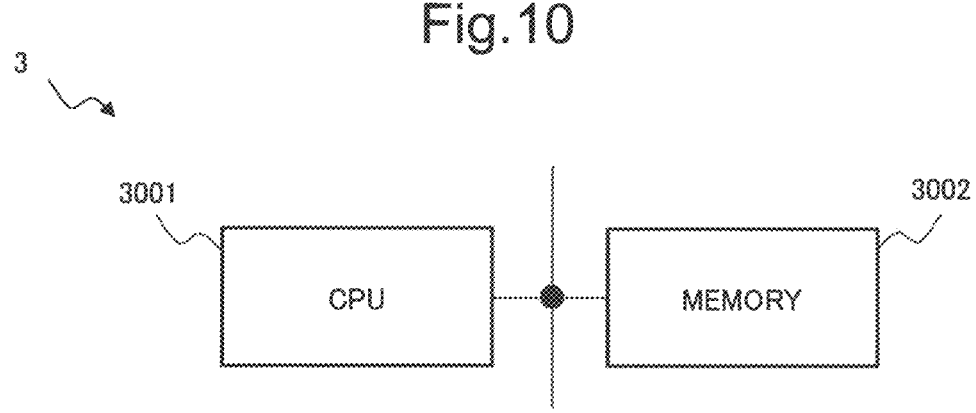
FIG. 10 is a view illustrating an example of a hardware configuration of the image diagnosis device as the third example embodiment.

Here, the image diagnosis device 3 can be composed of hardware elements as illustrated in FIG. 10. In FIG. 10, the image diagnosis device 3 is composed of a computer device including a CPU 3001 and a memory 3002. The memory 3002 is composed of a RAM, a ROM, an auxiliary storage device, etc. In this case, the CNN configuration storage unit 31 and parameter storage unit 32 are composed of the memory 3002. In addition, the CNN identification unit 38 is composed of the CPU 3001 which reads in a computer program stored in the memory 3002, and executes the computer program. Note that the hardware configuration of the image diagnosis device 3 and each functional block thereof is not limited to the above-described configuration. In addition, the image diagnosis device 3 may be composed of an identical computer device to the image diagnosis learning device 1, or may be composed of a different computer device from the image diagnosis learning device 1.

The CNN configuration storage unit 31 stores information representing the same network configuration as the CNN that was used by the image diagnosis learning device 1 as the first example embodiment.

The parameter storage unit 32 stores the parameters of the CNN, which were updated by applying the image diagnosis learning device 1 as the first example embodiment to one or a plurality of images for learning. For example, such parameters are the weight and bias in the CNN. It is preferable that the parameters of the CNN, which are stored in the parameter storage unit 32, are parameters which were updated by applying the image diagnosis learning device 1 to images for learning, which were obtained from a greater number of endoscopic images.

The CNN identification unit 38 executes calculation by inputting the information based on the diagnosis subject image to the CNN, by using the parameters of the CNN, which are stored in the parameter storage unit 32. Then, the CNN identification unit 38 identifies an abnormal region in the diagnosis subject image, based on the calculation result of the CNN.

Figure 11:
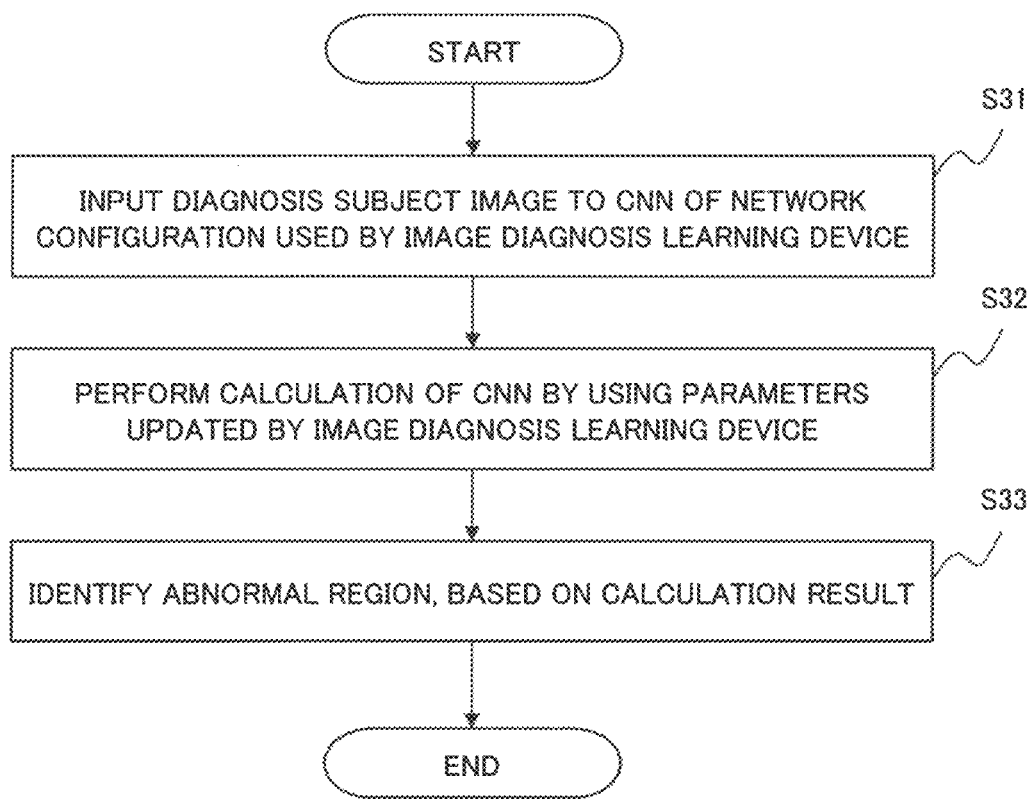
FIG. 11 is a flowchart for describing an operation of the image diagnosis device as the third example embodiment.

FIG. 11 illustrates the operation of the image diagnosis device 3 with the above-described configuration.

In FIG. 11, to start with, the CNN identification unit 38 inputs the diagnosis subject image to the CNN of the network configuration which was used by the image diagnosis learning device 1 as the first example embodiment (step S31).

Next, the CNN identification unit 38 executes the calculation of the CNN by using the parameters of the CNN, which were updated by the image diagnosis learning device 1 of the first example embodiment (step S32).

Subsequently, the CNN identification unit 38 identifies an abnormal region in the diagnosis subject image, based on the calculation result of the CNN (step S33).

By the above, the image diagnosis device 3 terminates the operation.

Next, the advantageous effects of the third example embodiment will be described.

The image diagnosis device as the third example embodiment can more precisely detect an abnormal region, even when a region in which an intended diagnosis subject is not sufficiently photographed is included in a diagnosis subject image in which the diagnosis subject is photographed by a normal photography method that is not implemented by a special function.

The reason for this is described. In the present example embodiment, the CNN configuration storage unit stores the network configuration of the CNN that was used by the image diagnosis learning device as the first example embodiment. In addition, the parameter storage unit stores the parameters of the CNN, which were updated by the image diagnosis learning device as the first example embodiment. Further, the CNN identification unit inputs the diagnosis subject image to the CNN of the network configuration which was used by the image diagnosis learning device as the first example embodiment. Then, the CNN identification unit executes the calculation of the CNN by using the parameters of the CNN which were updated by the image diagnosis learning device as the first example embodiment, and identifies the abnormal region in the diagnosis subject image, based on the result of the calculation. The above is the reason.

Here, the parameters of the CNN, which were updated by the image diagnosis learning device as the first example embodiment, are learned by suppressing the influence due to the inappropriate region in the image for learning in which the diagnosis subject is photographed. Accordingly, in the present example embodiment, since the CNN using such parameters is applied to the diagnosis subject image, the abnormal region can be identified with high precision.

Fourth Example Embodiment

Next, a fourth example embodiment will be described in detail with reference to the accompanying drawings. In the present example embodiment, a visceral wall surface is applied as a diagnosis subject. In addition, in the present example embodiment, a description is given of an example of an image diagnosis device which identifies a candidate for a lesion in an endoscopic image, by using the parameters of the CNN which were updated by the second example embodiment. Note that in the drawings which are referred to in the description of the present example embodiment, the identical configuration and similarly operating steps to the third example embodiment are denoted by the identical reference signs, and a detailed description thereof in the present example embodiment is omitted.

Figure 12:
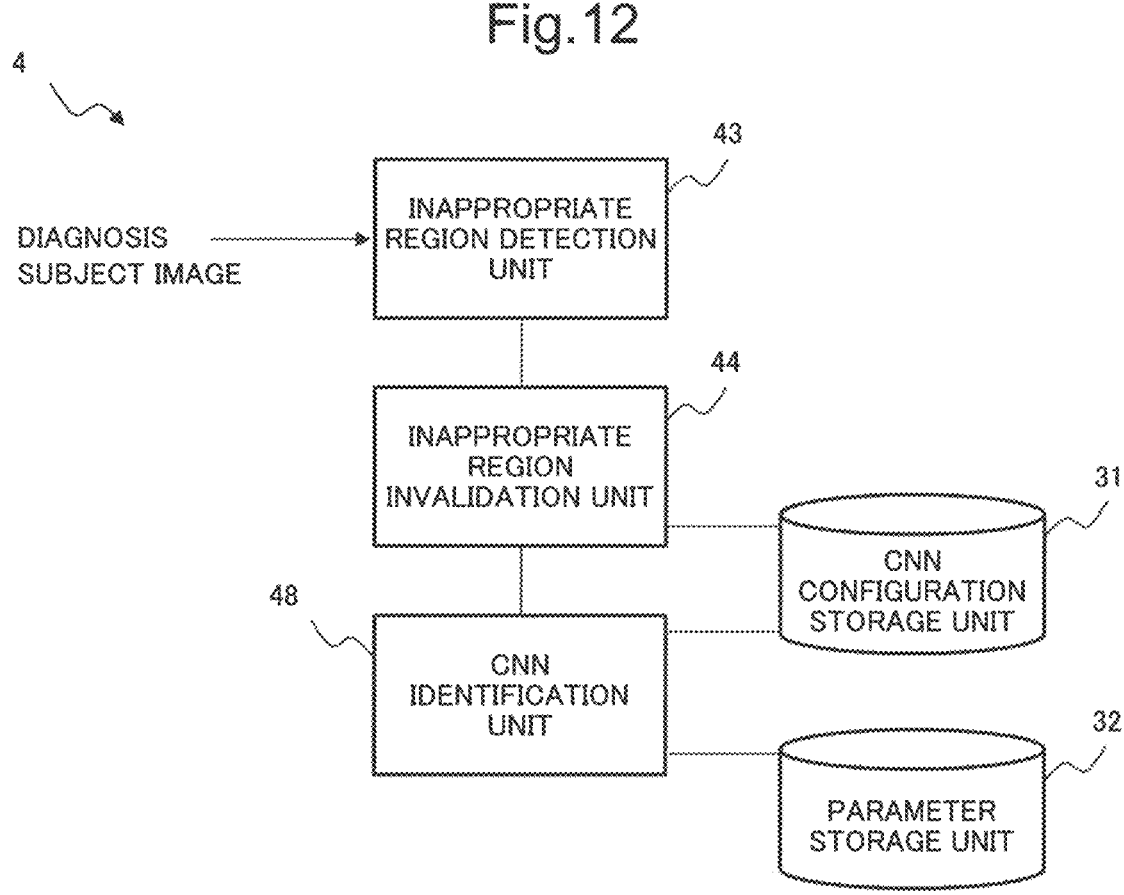
FIG. 12 is a block diagram illustrating a configuration of an image diagnosis device as a fourth example embodiment.

To begin with, FIG. 12 illustrates a configuration of an image diagnosis device 4 as the fourth example embodiment. In FIG. 12, the image diagnosis device 4 differs from the image diagnosis device 3 as the third example embodiment, in that the image diagnosis device 4 includes a CNN identification unit 48 in place of the CNN identification unit 38, and further includes an inappropriate region detection unit 43 and an inappropriate region invalidation unit 44. Note that it is assumed that the network configuration of the CNN and the updated parameters, which were used by the image diagnosis learning device as the second example embodiment, are stored in the CNN configuration storage unit 31 and parameter storage unit 32.

Here, the image diagnosis device 4 and the functional blocks thereof can be composed of similar hardware elements to the image diagnosis device 3 as the third example embodiment described with reference to FIG. 10. However, the hardware configuration of the image diagnosis device 4 and the functional blocks thereof is not limited to the above-described configuration.

The inappropriate region detection unit 43 detects a shine part as an inappropriate region in the diagnosis subject image. Since the details of the process of detecting a shine part are the same as with the inappropriate region detection unit 23 in the second example embodiment, a description thereof in the present example embodiment is omitted. For example, the inappropriate region detection unit 43 may execute a process of detecting a shine part, by using a patch image that is a partial region of the diagnosis subject image.

The inappropriate region invalidation unit 44 invalidates a unit corresponding to a shine part, among the units of the input layer of the CNN to which the diagnosis subject image was input. For example, the inappropriate region invalidation unit 44 may execute the process of invalidation with respect to a patch image that is a partial region of the diagnosis subject image. In this case, the inappropriate region invalidation unit 44 may invalidate a unit corresponding to a shine part, among the units of the input layer of the CNN to which the patch image is input. Note that the network configuration of the CNN, to which the diagnosis subject image or the patch image thereof is input, is stored in the CNN configuration storage unit 31. Since the details of the process of invalidating the unit corresponding to the shine part are the same as with the inappropriate region invalidation unit 14 in the first example embodiment, a description thereof in the present example embodiment is omitted.

The CNN identification unit 48 identifies a non-lesion part or the kind of lesion part with respect to the diagnosis subject image. Specifically, the CNN identification unit 48 executes Forward calculation of the CNN by applying the parameters of the CNN stored in the parameter storage unit 32 to the CNN in the state in which the diagnosis subject image was input and the shine part was invalidated. For example, the CNN identification unit 48 may execute identification with respect to a patch image that is a partial image of the diagnosis subject image. In this case, the CNN identification unit 48 may execute Forward calculation of the CNN by applying the parameters of the CNN stored in the parameter storage unit 32 to the CNN in the state in which the patch image was input and the shine part was invalidated. Then, the CNN identification unit 48 outputs, as an identification result of the CNN, lesion class information of the visceral wall surface which is photographed in the patch image.

Here, by executing the Forward calculation of the CNN, an identification score for each lesion class is output from the CNN. For example, the CNN identification unit 48 may execute a SoftMax function on the identification score for each lesion class, thereby converting the identification score to a score of a real value in a range of between 0 and 1. Thereby, the CNN identification unit 48 can calculate a score indicative of the likelihood of each lesion class with respect to the visceral wall surface that is photographed in the patch image.

In addition, when the CNN identification unit 48 executed identification with respect to patch images that are respective partial images of the diagnosis subject image, the CNN identification unit 48 may output a score for each patch image. For example, the CNN identification unit 48 may cause a display device (not illustrated) to display the score for each patch image as a score map indicative of the likelihood of the lesion class in the diagnosis subject image. Here, the score map is an image including, as an image, the score of each patch image at the position of the patch image in the diagnosis subject image. In addition, the CNN identification unit 48 may output such a score map by superimposing the score map on the diagnosis subject image.

The operation of the image diagnosis device 4 with the above-described configuration will be described with reference to FIG. 13. Here, it is assumed that the image diagnosis device 4 operates with respect to each patch image that is cut out of an endoscopic image of a diagnosis subject.

Figure 13:
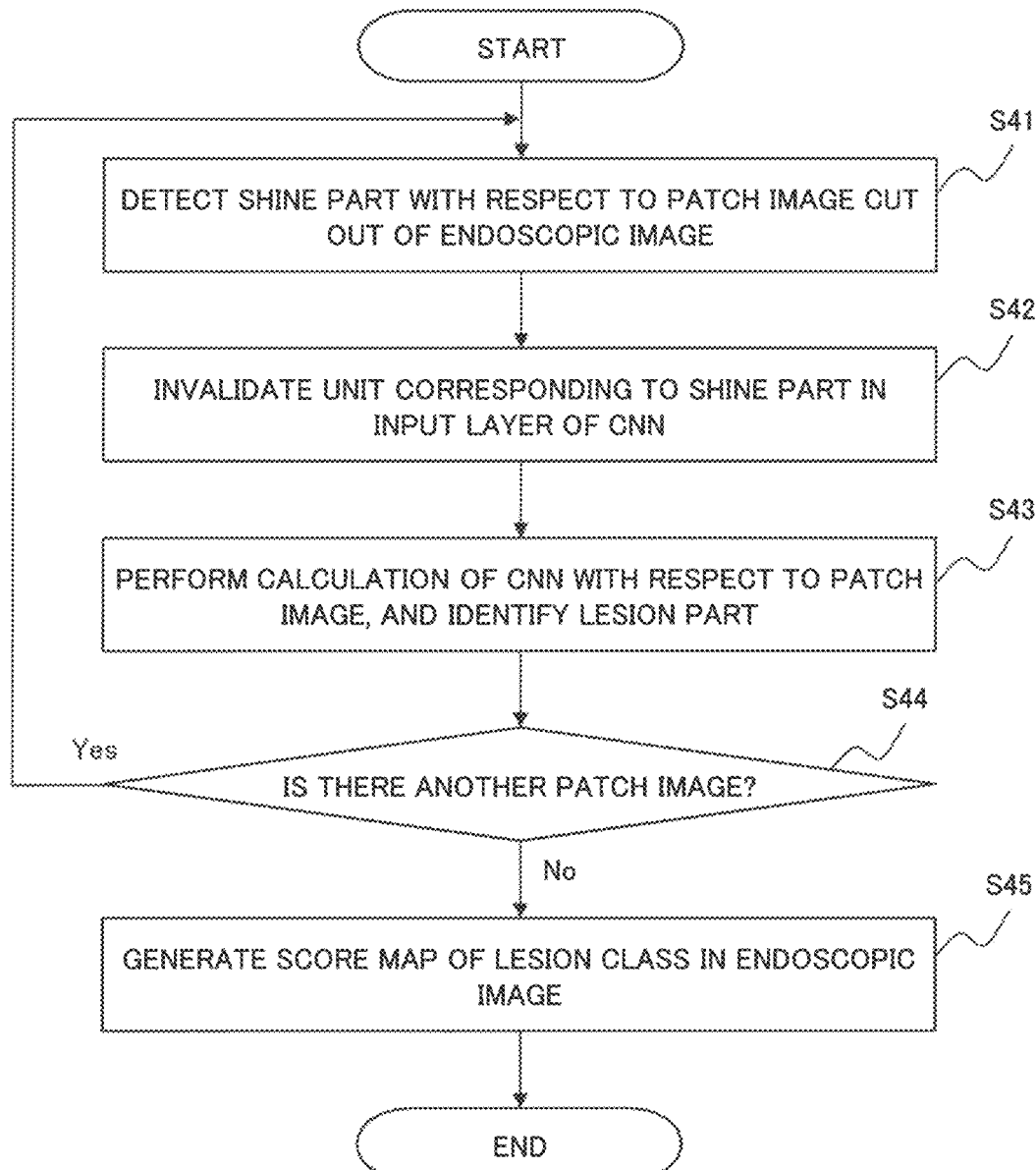
FIG. 13 is a flowchart for describing an operation of the image diagnosis device as the fourth example embodiment.

In FIG. 13, to start with, the inappropriate region detection unit 43 detects a shine part in the patch image that was cut out of endoscopic image (step S41).

Next, the inappropriate region invalidation unit 44 temporarily invalidates a unit corresponding to the shine part, among the units of the input layer of the CNN to which the patch image was input (step S42).

Subsequently, the CNN identification unit 48 executes Forward calculation of the CNN in the state in which the unit of the input layer, which corresponds to the shine part, is temporarily invalidated. Thereby, a score for each lesion class is output from the CNN (step S43).

Here, if there is another patch image included in the endoscopic image (Yes in step S44), the image diagnosis device 4 repeats the operation from step S41.

On the other hand, if there is no other patch image included in the endoscopic image (No in step S44), the CNN identification unit 48 outputs the likelihood of a lesion for each patch image (step S45). Note that, as described above, for example, the CNN identification unit 48 may cause the display device to display the likelihood of the lesion for each patch image as a score map score for displaying the likelihood of the lesion at the position of the patch image in the diagnosis subject image, by superimposing the score map on the endoscopic image. The CNN identification unit 48 may include this display device. Thereby, such an advantage is obtained that the location of a lesion part is more easily confirmed by visual observation by a human.

Next, the advantageous effects of the fourth example embodiment will be described.

The image diagnosis device as the present example embodiment can more precisely detect a region with a possibility of a lesion part, even when a shine part is included in an endoscopic image in which a visceral wall surface is photographed by a normal photography method which is not implemented by a special function such as NBI endoscope or a magnifying endoscope.

The reason for this is described. In the present example embodiment, the CNN configuration storage unit and parameter storage unit store the network configuration of the CNN and the updated parameters, which were used by the image diagnosis learning device as the second example embodiment. In addition, the inappropriate region detection unit detects the shine part in the endoscopic image. Further, the inappropriate region invalidation unit inputs the patch image of the endoscopic image to the CNN of the network configuration used by the image diagnosis learning device as the second example embodiment, and temporarily invalidates a unit corresponding to the shine part in the input layer. Further, the CNN identification unit executes identification by executing the Forward calculation of the CNN in the state in which the unit corresponding to the shine part is temporarily invalidated, by using the parameters updated by the image diagnosis learning device as the second example embodiment. The above is the reason.

In this manner, the present example embodiment executes the identification by the CNN having the same network configuration as the CNN which was used in the second example embodiment, by using the parameters learned by the second example embodiment. Thus, the present example embodiment can correctly detect the likelihood of a lesion in an endoscopic image, even when the endoscopic image is a general endoscopic image which is not acquired by an NBI endoscope or a magnifying endoscope.

In addition, the present example embodiment executes identification by using the parameters learned in the state in which a shine part is eliminated. Thus, the present example embodiment can execute identification with high precision, even when a shine part is eliminated from an identification subject image. In this manner, since the present example embodiment executes identification by automatically detecting a shine part and invalidating the corresponding unit in the input layer of the CNN, the present example embodiment can execute the identification by suppressing the influence of the abnormal value occurring at the shine part in the diagnosis subject image. Specifically, in the present example embodiment, even from the data including a shine part in the diagnosis subject image, the identification can be executed by suppressing the influence of the shine part as much as possible.

Note that as the network configuration of the CNN used in the present example embodiment, the example was described in which the same network configuration as the CNN used in the second example embodiment is stored in the CNN configuration storage unit. Aside from this, the CNN configuration storage unit may store a configuration from the input layer to an intermediate layer, from which the feature is extracted, in the network configuration of the CNN used in the second example embodiment. For example, of the network configuration of the CNN used in the second example embodiment, a configuration composed of the Convolution layer and Pooling layer except the fully-connected layer may be stored. In this case, the CNN configuration storage unit may store, as the parameters, at least parameters necessary for the calculation from the input layer to the intermediate layer. In this case, in the present example embodiment, the information that is output from the CNN identification unit can be regarded as a numeral value sequence indicative of the feature which is effective for identifying the lesion class. In this case, the identification of the lesion class is enabled by the numeral value sequence, which is the output of the present example embodiment, being input to an arbitrary identification device such as a support vector machine.

In addition, of the network configuration of the CNN used in the second example embodiment, when the configuration from the input layer to the above-described intermediate layer is used, the CNN identification unit may input to the CNN, not the patch image that is cut out of the endoscopic image, but the entire area of the endoscopic image. In this case, the information that is output from the CNN identification unit is the feature which is effective for identifying each lesion class in the endoscopic image. Then, the CNN identification unit may output, as a score map indicative of the possibility of each lesion class in the endoscopic image, the calculation results up to the intermediate layer, by representing the calculation result as an image in accordance with the position in the endoscopic image. In this manner, when the entire area of the diagnosis subject image is input, the present example embodiment can generate the score map indicative of the possibility of the lesion class at high speed by reducing the calculation amount, compared to the case of repeating the identification process for each patch image while scanning the diagnosis subject image.

Note that, in each of the above-described example embodiments, the example was mainly described in which the respective pixels of the image for learning or the diagnosis subject image are allocated to the respective units of the input layer of the CNN. Aside from this, information, in which the image for learning or the diagnosis subject image was processed in advance, may be input to the respective units of the input layer. For example, by the image for learning or the diagnosis subject image being processed by a Sobel operator, Laplacian operator or the like, the respective pixels of a primary differential image or secondary differential image of luminance may be input to the respective units of the input layer. In this case, in the first, second and fourth example embodiments, the inappropriate region invalidation unit may invalidate, among the units of the input layer, a unit to which a pixel of a differential image is input, the pixel of the differential image corresponding to an inappropriate region detected in the image for learning or diagnosis subject image before being processed.

Additionally, in the above-described second and fourth embodiments, the example was mainly described in which the visceral wall surface is applied as the diagnosis subject, and the image based on the endoscopic image is applied as the diagnosis subject image. Aside from this, in these example embodiments, a diagnosis subject image, in which some other subject is applied as the diagnosis subject, may be used. Besides, in these example embodiments, the example was mainly described in which a shine part is applied as an inappropriate region. Aside from this, in these example embodiments, some other region, which is not suitable for the identification of an abnormal region, may be applied as the inappropriate region.

Additionally, in each of the above-described example embodiments, aside from the above-described calculation methods, various kinds of publicly known calculation methods, which are applicable to the CNN in which a part of units is invalidated, can be applied to the loss value calculation unit and parameter updating unit.

Additionally, in each of the above-described example embodiments, the example was mainly described in which the respective functional blocks of the image diagnosis learning device and image diagnosis device are realized by the CPU which executes computer programs stored in the memory. Aside from this, a part or all of the functional blocks, or a combination thereof, may be realized by purpose-specific hardware.

Additionally, in each of the above-described embodiments, the functional blocks of the image diagnosis learning device or image diagnosis device may be realized by being distributed into a plurality of devices.

Additionally, in each of the above-described embodiments, the operation of the image diagnosis learning device or image diagnosis device, which was described with reference to the flowcharts, may be stored as a computer program in a storage device (recording medium). Then, the CPU may read out and execute the computer program. In such a case, the operation is constituted by the code of the computer program or the recording medium.

Additionally, the above-described example embodiments can be implemented by being combined as needed.

Additionally, the disclosed subject matter of the present invention is not limited to the above-described example embodiments, and can be implemented in various modes.

REFERENCE SIGNS LIST

1, 2 Image diagnosis learning device
3, 4 Image diagnosis device
11, 31 CNN configuration storage unit
12, 32 Parameter storage unit
13, 23, 43 Inappropriate region detection unit
14, 44 Inappropriate region invalidation unit
15 Loss value calculation unit
16 Parameter updating unit
27 Disturbance unit
38, 48 CNN identification unit
1001, 3001 CPU
1002, 3002 Memory

The invention claimed is:
1. An image diagnosis learning device comprising:
a CNN configuration storage that stores a network configuration of a convolutional neural network, CNN;
a parameter storage that stores parameters of a learning subject in the CNN;
a memory storing instructions; and
at least one processor configured to process the instructions to:
detect, based on a predetermined criterion, an inappropriate region which is a region inappropriate for identification of an abnormal region where a diagnosis subject has a possibility of abnormality, in an image for learning in which the diagnosis subject is photographed;
invalidate a unit corresponding to the inappropriate region, among units of an input layer in the network configuration of the CNN to which the image for learning has been input;
perform calculation of the CNN by using the parameters in a state where the unit of the input layer, which corresponds to the inappropriate region, has been invalidated, and a loss value based on a result of the calculation and information, the information indicating abnormality of the diagnosis subject and given to the image for learning in advance; and
update the parameters of the parameter storage-, based on the loss value.

2. The image diagnosis learning device according to claim 1,
wherein the processor is further configured to process the instructions to generate the image for learning by executing a disturbance process on a learning sample of an image in which the diagnosis subject is photographed.

3. An image diagnosis device comprising:
a parameter storage storing the parameters of the CNN, which were updated by applying the image diagnosis learning device according to claim 1 to one or a plurality of images for learning;
a CNN configuration storage that stores a network configuration of the CNN used by the image diagnosis learning device when the parameters were updated; and
a memory storing instructions; and
at least one processor configured to process the instructions to:
input information based on the diagnosis subject image, in which the diagnosis image is photographed, to the CNN, and perform calculation, thereby identifying an abnormal region where the diagnosis subject has a possibility of abnormality in the diagnosis subject image.

4. The image diagnosis device according to claim 3, further comprising:
wherein the image diagnosis device processor is further configured to process the instructions to:
detect, based on a predetermined criterion, the inappropriate region in the diagnosis subject image; and
invalidate a unit corresponding to the inappropriate region, among units of an input layer in the CNN to which the diagnosis subject image has been input,
perform calculation of the CNN in a state in which the unit of the input layer, which corresponds to the inappropriate region, has been invalidated, thereby identifying the abnormal region in the diagnosis subject image.

5. The image diagnosis device according to claim 3,
wherein the image diagnosis device processor is further configured to process the instructions to perform the identification by using the CNN with respect to each of partial regions included in the diagnosis subject image, thereby outputting an identification result for each partial region.

6. The image diagnosis device according to claim 3,
wherein the image diagnosis device processor is further configured to process the instructions to:
input an entire area of the diagnosis subject image to the CNN, and
perform calculation of the CNN by using a configuration up to a layer from which a feature is extracted, in the network configuration of the CNN, thereby outputting a feature relating to the abnormal region in the diagnosis subject image.

7. A method in which a computer device executes:
detecting, based on a predetermined criterion, an inappropriate region which is a region inappropriate for identification of an abnormal region where a diagnosis subject has a possibility of abnormality, in an image for learning in which the diagnosis subject is photographed;
invalidating a unit corresponding to the inappropriate region, among units of an input layer in a network configuration of a convolutional neural network, CNN, to which the image for learning has been input;
performing calculation of the CNN in a state where the unit of the input layer, which corresponds to the inappropriate region, has been invalidated, and calculating a loss value based on a result of the calculation and information, the information indicating abnormality of the diagnosis subject and given to the image for learning in advance; and
updating parameters of a learning subject in the CNN, based on the loss value.

8. A method in which a computer device executes,
by using the parameters of the CNN, which were updated by executing the method according to claim 7 on one or a plurality of images for learning, and a network configuration of the CNN used when the parameters were updated,
inputting information based on the diagnosis subject image, in which the diagnosis image is photographed, to the CNN, and performing calculation, thereby identifying an abnormal region where the diagnosis subject has a possibility of abnormality in the diagnosis subject image.

9. A non-transitory computer readable recording medium for storing a program which causes a computer device to execute:
detecting, based on a predetermined criterion, an inappropriate region which is a region inappropriate for identification of an abnormal region where a diagnosis subject has a possibility of abnormality, in an image for learning in which the diagnosis subject is photographed;
invalidating a unit corresponding to the inappropriate region, among units of an input layer in a network configuration of a convolutional neural network, CNN, to which the image for learning has been input;
performing calculation of the CNN in a state where the unit of the input layer, which corresponds to the inappropriate region, has been invalidated, and calculating a loss value based on a result of the calculation and information, the information indicating abnormality of the diagnosis subject and given to the image for learning in advance; and
updating parameters of a learning subject in the CNN, based on the loss value.

10. A non-transitory computer readable recording medium for storing a program which causes a computer device to execute,
by using the parameters of the CNN, which were updated by causing the computer device to execute the program stored in the recording medium according to claim 9 on one or a plurality of images for learning, and a network configuration of the CNN used when the parameters were updated,
inputting information based on the diagnosis subject image, in which the diagnosis image is photographed, to the CNN, and performing calculation, thereby identifying an abnormal region where the diagnosis subject has a possibility of abnormality in the diagnosis subject image.

\* \* \* \* \*